(12) United States Patent
Hu et al.

(10) Patent No.: US 9,211,393 B2
(45) Date of Patent: Dec. 15, 2015

(54) DISTAL COOLING DISTRIBUTION SYSTEM FOR A MEDICAL DEVICE

(75) Inventors: Yixin Hu, Montreal (CA); Vladimir Tzonev, Kirkland (CA); Teresa Ann Mihalik, Montréal (CA); Benoit Thibault, Coteau-du-Lac (CA); Dan Wittenberger, L'lle Bizard (CA); Miriam Lane, Dollard-des-Ormeaux (CA); Cristian Petre, Laval (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 2465 days.

(21) Appl. No.: 11/476,416

(22) Filed: Jun. 28, 2006

(65) Prior Publication Data

US 2008/0097373 A1 Apr. 24, 2008

Related U.S. Application Data

(63) Continuation-in-part of application No. 11/446,932, filed on Jun. 5, 2006, now Pat. No. 7,871,395.

(51) Int. Cl.
*A61M 25/10* (2013.01)
*A61M 25/00* (2006.01)
*A61M 25/01* (2006.01)
*A61B 18/02* (2006.01)
(Continued)

(52) U.S. Cl.
CPC ............ *A61M 25/1025* (2013.01); *A61B 18/02* (2013.01); *A61B 2017/22051* (2013.01); *A61B 2018/0022* (2013.01); *A61B 2018/0212* (2013.01); *A61M 2025/0004* (2013.01); *A61M 2025/0175* (2013.01); *A61M 2025/1061* (2013.01)

(58) Field of Classification Search
CPC ............. A61M 2025/0004; A61M 2025/0175; A61M 25/1025; A61M 2025/1061
USPC ............. 604/103.03, 164.01, 164.03, 164.09, 604/164.13, 264, 523, 528, 915, 93.01, 604/95.01, 95.03, 95.04, 96.01
See application file for complete search history.

(56) References Cited

U.S. PATENT DOCUMENTS

| 3,561,445 | A | 2/1971 | Katerndahl |
| 3,826,256 | A | 7/1974 | Smith |

(Continued)

FOREIGN PATENT DOCUMENTS

| EP | 1398056 A1 | 3/2004 |
| WO | 0182810 A1 | 11/2001 |
| WO | 0246080 A1 | 6/2002 |

*Primary Examiner* — Kevin C Sirmons
*Assistant Examiner* — Shefali Patel
(74) *Attorney, Agent, or Firm* — Christopher & Weisberg, P.A.

(57) ABSTRACT

The present invention may include a medical device having a handle, a catheter coupled to the handle, and an expandable element coupled to the catheter. The medical device may also include first and second elongate bodies that traverse a length of the handle and the catheter. A housing may be disposed within the handle, with the housing defining a first opening able to receive a portion of the first elongate body, a second opening able to receive a portion of the second elongate body, and a third opening opposite the first and second openings able to receive a portion of both the first and second elongate bodies. A separation element may be disposed within the housing, with the separation element defining a path able to receive a portion of the second elongate body, and whereby a portion of the first elongate body forms a loop around the separation element.

14 Claims, 6 Drawing Sheets

(51) Int. Cl.
  *A61B 17/22* (2006.01)
  *A61B 18/00* (2006.01)

(56) References Cited

U.S. PATENT DOCUMENTS

| | | | |
|---|---|---|---|
| 4,151,648 A | 5/1979 | Hirth | |
| 4,160,451 A | 7/1979 | Chittenden | |
| 4,255,076 A | 3/1981 | Svenning | |
| 4,526,175 A | 7/1985 | Chin et al. | |
| 4,637,404 A | 1/1987 | Gessman | |
| 4,713,059 A | 12/1987 | Bickelhaupt et al. | |
| 4,850,974 A | 7/1989 | Bickelhaupt et al. | |
| 5,064,415 A | 11/1991 | Walder et al. | |
| 5,460,608 A * | 10/1995 | Lodin et al. | 604/103.09 |
| 5,800,393 A | 9/1998 | Sahota | |
| 5,855,567 A * | 1/1999 | Reesemann | 604/171 |
| 5,868,735 A * | 2/1999 | Lafontaine | 606/21 |
| 5,935,102 A | 8/1999 | Bowden et al. | |
| 5,975,120 A | 11/1999 | Novosel | |
| 6,086,008 A * | 7/2000 | Gray et al. | 242/388.6 |
| 6,231,564 B1 | 5/2001 | Gambale | |
| 6,258,061 B1 | 7/2001 | Drasler et al. | |
| 6,283,959 B1 * | 9/2001 | Lalonde et al. | 606/21 |
| 6,334,457 B1 | 1/2002 | Baker, IV | |
| 6,551,274 B2 * | 4/2003 | Heiner | 604/113 |
| 6,569,158 B1 * | 5/2003 | Abboud et al. | 606/20 |
| 6,572,610 B2 | 6/2003 | Kovalcheck et al. | |
| 6,623,471 B1 | 9/2003 | Barbut | |
| 6,682,473 B1 | 1/2004 | Matsuura et al. | |
| 6,867,980 B2 | 3/2005 | Wrycraft | |
| 6,936,042 B2 | 8/2005 | Wallace et al. | |
| 2001/0056257 A1 | 12/2001 | Drasler et al. | |
| 2002/0065512 A1 | 5/2002 | Fjield et al. | |
| 2002/0143238 A1 | 10/2002 | Hino et al. | |
| 2004/0006333 A1 | 1/2004 | Arnold et al. | |
| 2004/0044334 A1 * | 3/2004 | LaFontaine | 606/21 |
| 2004/0204628 A1 | 10/2004 | Rovegno | |
| 2005/0020940 A1 | 1/2005 | Opie et al. | |
| 2005/0042588 A1 | 2/2005 | Wallaker | |
| 2006/0004286 A1 | 1/2006 | Chang et al. | |

* cited by examiner

DISTAL COOLING DISTRIBUTION SYSTEM FOR A MEDICAL DEVICE

REFERENCE TO RELATED APPLICATION

This application is a continuation-in-part of pending Utility patent application Ser. No. 11/446,932 filed Jun. 5, 2006, by Yixin Hu, et al., entitled SERVICE LOOP, the entirety of which is incorporated herein by reference.

STATEMENT REGARDING FEDERALLY SPONSORED RESEARCH OR DEVELOPMENT n/a

FIELD OF THE INVENTION

The present invention provides an apparatus for accommodating and managing lengths of conduit in a medical device, as well as for maintaining a spatial relationship between movable components of the medical device.

BACKGROUND OF THE INVENTION

Medical devices used in surgery for performing ablation, dilation, and the like often include multiple conduits and connectors for providing both fluid flow and electrical connections between the device and a fluid supply and/or control console, as well as providing for steering or navigation of the device over a guidewire. In particular, some surgical procedures involve the expansion or inflation of an inflatable element, such as a balloon, which may be disposed on a catheter or similar device. The catheter may be inserted through the vasculature of a patient, applied directly to contact a tissue surface, etc. Regardless of the particular approach, the expansion/inflation of the balloon may result in alternating periods of slack and tension in the conduits providing fluid flow, electrical connections, and the like, which can cause axial and longitudinal movement of the conduits. Such movement may result in the undesired kinking and/or tangling of multiple conduits of a device, whereby the kinking may degrade or prevent the performance of the device, causing a reduction in the overall effectiveness and/or usability of the device for certain medical procedures.

In addition, where a medical device includes a balloon, and the aforementioned components of the device experience axial movement, an inflation tube providing an inflation fluid to expand the balloon may be axially displaced. Should such axial displacement occur during an inflation sequence, there may be a risk that inflation fluid will be directed towards an undesirable portion of the balloon and/or surrounding structures of the medical device. Moreover, should the inflation fluid perform an additional function, such as providing a particular thermal condition at a specific portion of the balloon, then axial displacement of the inflation tube may disrupt and/or reduce the effectiveness or achievement of the desired condition.

In light of the above, it is desirable to provide for an apparatus for accommodating and managing lengths of conduit in a medical device to prevent unwanted kinking and/or damage to components, while further facilitating and easing overall use of the device. Moreover, it would be desirable to ensure the desired location and/or placement of moving parts of a medical device during a particular sequence of operation of the device.

SUMMARY OF THE INVENTION

The present invention advantageously provides a method and system for accommodating and managing lengths of conduit in a medical device to prevent unwanted kinking and/or damage to components, while further facilitating and easing overall use of the device. In addition, he present invention advantageously ensure the desired location and/or placement of moving parts of a medical device during a particular sequence of operation of the device.

In particular, the present invention provides a medical device having a handle, a catheter coupled to the handle, and an expandable element coupled to the catheter. The medical device may also include a first elongate body, such as a guidewire lumen, wherein the first conduit traverses a length of the handle and catheter. A second elongate body, such as a fluid injection lumen, may also traverse a length of the handle and catheter. The second elongate body may be affixed to the first elongate body at a location having a predetermined spatial relationship to a portion of the expandable element, such that the spatial relationship is substantially maintained when the expandable element proceeds form an inflated state to an uninflated state.

In addition, a housing may be disposed within the handle, where the housing defines a first opening able to receive a portion of the first conduit, a second opening able to receive a portion of the second conduit, and a third opening opposite the first and second openings, such that the third opening is able to receive a portion of both the and second conduits. The present invention may further include a separation element disposed within the housing, with the separation element defining a channel able to receive a portion of the second conduit, and whereby a portion of the first conduit forms a loop around the separation element. In addition, the separation element may be rotatably coupled to the housing as to provide a reel of reserve conduit length that may dispensed upon experiencing a tension along the length of the conduit.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
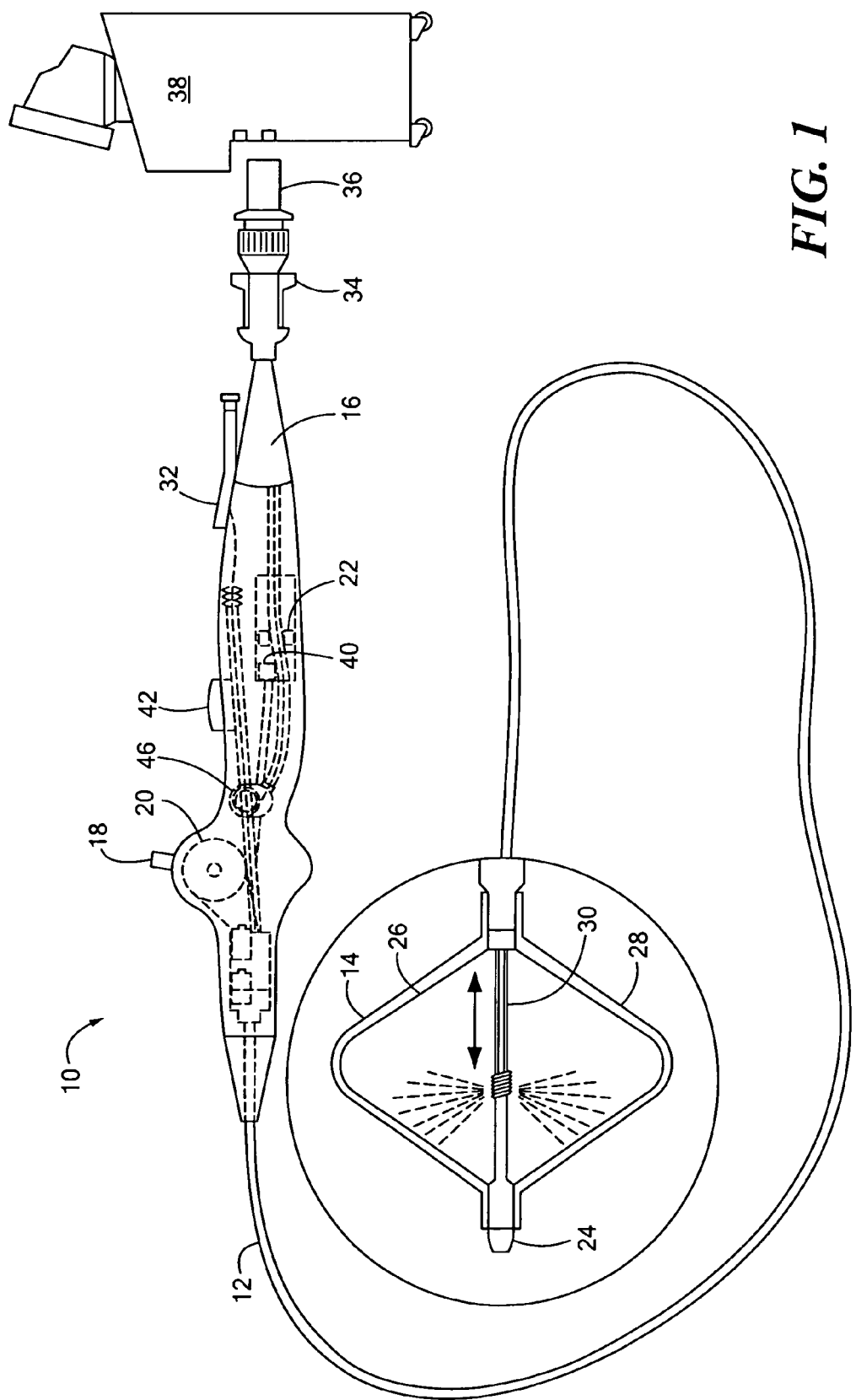
FIG. 1 illustrates a catheter system in accordance with an embodiment of the present invention.
Figure 2:
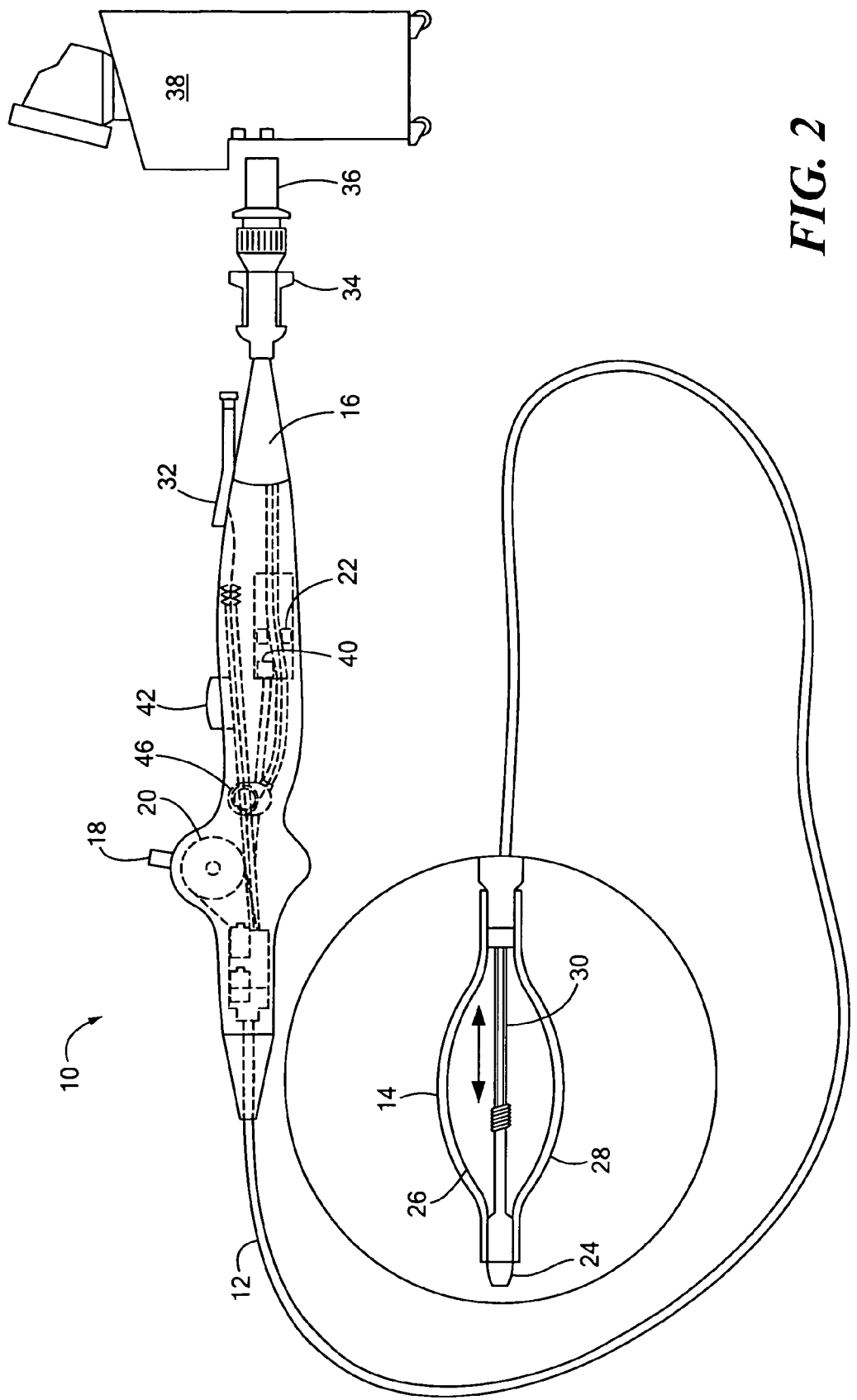
FIG. 2 shows an additional view of a catheter system in accordance with an embodiment of the present invention.

FIGS. 1 and 2 illustrate an exemplary system for performing a surgical procedure, including ablation, dilation, or the like. The system includes a medical device 10, which may include an elongate, highly flexible catheter that may be suitable for passage through the vasculature. The catheter may include a catheter body 12 having a distal end with an expandable element 14 at or proximal to the distal end. The distal end and the expandable element 14 are shown magnified and are described in greater detail below. The catheter body 12 has a proximal end that is mated to a handle 16, where the handle 16 may include an element such as a lever or knob 18 for manipulating the catheter body 12 and/or additional components of the medical device 10. For example, a pull wire with a proximal end and a distal end may have its distal end anchored to the catheter at or near the distal end. The proximal end of the pull wire may be anchored to an element such as a cam 20 in communication with and responsive to the lever. The handle 16 can further include circuitry 22 for identification and/or use in controlling of the ablation catheter or another component of the system.

Continuing to refer to FIGS. 1 and 2, the medical device 10 can also include one or more elongate bodies disposed within a portion of the handle 16, which may further extend along a length of the catheter. As used herein, the term "elongate body" is used to describe any structure and/or element for transmitting, communicating, and or channeling fluid, electricity, mechanical force, or the like, and may include, but is not limited to, tubing, piping, wiring, cable, and/or fiber optic elements.

A first elongate body 24, such as a guidewire lumen, may be movably disposed within the catheter body 12. The first elongate body 24 may define a distal portion as well as a proximal portion, with a length therebetween extending along at least a portion of the catheter body 12.

As mentioned above, the medical device 10 of the present invention may further include an expandable element 14 defining a proximal end and a distal end, where the expandable element 14 has an inflated state and an uninflated state. The expandable element 14 is shown as a double balloon having a first membrane 26 (e.g., inner balloon) contained or enclosed within a second membrane 28 (e.g., outer balloon), thereby defining an interface or junction between the first and second membranes. The second membrane 28 may provide a safeguard to prevent fluid from leaking out of the interior of the first membrane 26 and into the surrounding tissue should the first membrane 26 rupture or develop a leak. The expandable element 14 may be disposed about the catheter body 12 such that the proximal end of the expandable element 14 is coupled to the distal portion of the catheter body 12, with the distal end of the expandable element 14 being coupled to the distal portion of the first elongate body 24. As such, due to the movable nature of the first elongate body 24, any axial and/or longitudinal movement of the first elongate body 24 may act to tension or loosen the expandable element 14, i.e., extend or retract the expandable element 14 from a lengthened state to a shortened state during deflation or inflation, respectively. The movable nature of the first elongate body 24 and the potential corresponding configuration of the expandable element 14 is illustrated by the distal portion detail provided in FIGS. 1 and 2. The expandable element 14 may be any of a myriad of shapes, and may further include one or more layers to provide for puncture resistance, radiopacity, etc.

A second elongate body 30, such as a fluid supply tube or the like, for example, may also be movably disposed within at least a portion of the catheter body 12. The second elongate body 30 may define a proximal portion and a distal portion, and may be disposed within the catheter body 12 such that the distal portion of the second elongate body 30 is affixed to the distal portion of the first elongate body 24. Further, the second elongate body 30 may include one or more openings at its distal portion for providing fluid flow. The second elongate body 30 may be placed in fluid communication with a fluid supply in order to transport fluid from one or more openings in the proximal portion of the second elongate body 30 and towards the distal portion, which may be in proximity to the expandable element 14 of the medical device 10.

In particular, the coupling between the first and second elongate bodies may be located at a desired and/or pre-determined position between the proximal and distal ends of the expandable element 14. In particular, it may be desired to position and/or direct fluid flow out of the second elongate body 30 in accordance with a pre-determined and/or particular location of the expandable element 14. For example, in a procedure employing a coolant as a medium for expanding the expandable element 14 for providing thermal interaction between the device and a target tissue site, it may be desirable to affix the distal portion of the second elongate body 30 to the distal portion of the first elongate body 24 such that the coupling is in closer proximity to the distal end of the expandable element 14 than the proximal end of the expandable element 14, i.e., it may be desired to inject coolant towards the distal end of the expandable element 14 rather than the proximal end.

The location of the distal portion of the second elongate body 30 then remains relatively constant with respect to a particular portion of the expandable element 14, because even if the first elongate body 24 moves with respect to the catheter body 12, thereby tensioning or loosening the expandable element 14 as described above, the distal portion of the second elongate body 30 moves in accordance with the first elongate body 24. Accordingly, a substantially fixed spatial relationship is maintained between the distal coupling of the first and second elongate bodies and the expandable element 14, regardless of the particular stage of inflation the expandable balloon may be experiencing, or the axial movement of the first elongate body 24. This spatial relationship may be configured in virtually any pre-determined orientation depending on the particular application the medical device 10 may be used for, and is not limited to any particular spacing and/or dimension between the distal portion of the second elongate body 30 and the expandable element 14.

While the first and second elongate bodies may be coupled at their respective distal portions, the proximal portions of the first and second elongate bodies may be independent of each other, and coupled to other individual components of the medical device 10. For example, the handle 16 may be provided with a fitting 32 for receiving a guidewire that may be passed into the first elongate body 24. The handle 16 may also include connectors that are matable directly to a fluid supply/exhaust and control unit or indirectly by way of one or more umbilicals for providing fluid communication with the second elongate body 30. In the system illustrated, the handle 16 is provided with a first connector 34 that is matable with a co-axial fluid umbilical (not shown) and a second connector 36 that is matable with an electrical umbilical (not shown) that can further include an accessory box (not shown).

In an exemplary system, the fluid supply and exhaust, as well as various control mechanisms for the system may be housed in a single console 38. In addition to providing an exhaust function for the catheter fluid supply, the console 38 may also recover and/or re-circulate the fluid. A vacuum pump in the console 38 may create a low-pressure environment in one or more conduits within the catheter body 12 so that fluid is drawn into the conduit(s), away from the inner balloon, and towards the proximal end of the catheter. The vacuum pump may also be in fluid communication with the interface or junction of the first and second membranes of the expandable element 14 so that any fluid that leaks from the first membrane 26 is contained and aspirated. Additionally, the handle 16 may include one or more pressure sensors 40 to monitor the fluid pressure within the medical device 10.

In addition, an embodiment of the medical device 10 of the present invention may include an actuator element 42 that is movably coupled to the proximal portion of the catheter body 12 and/or the handle 16, and further coupled to the proximal portion of the first elongate body 24. Accordingly, manipulating the actuator element 42 in a longitudinal direction may cause the first elongate body 24 to slide towards either of the proximal or distal portions of the catheter body 12. As a portion of the expandable element 14 may be coupled to the first elongate body 24, manipulation of the actuator element 42 may further cause the expandable element 14 to be tensioned or loosened, depending on the direction of movement of the actuator element 42, and thus, the first elongate body 24. The actuator element 42 may include a thumb-slide, a push-button, a rotating lever, or other mechanical structure for providing a movable coupling to the catheter or handle 16.

Figure 3:
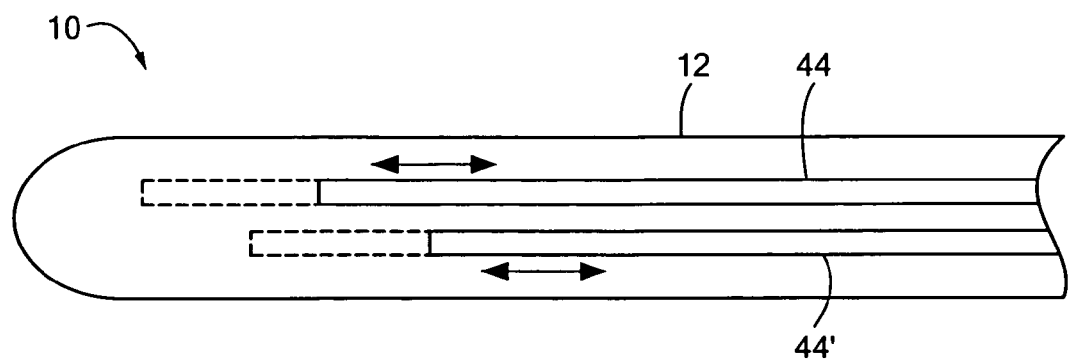
FIG. 3 provides a cross-sectional view of an embodiment of a medical device in accordance with the present invention.

An embodiment of a medical device 10 in accordance with the present invention may include a distal tip absent any expandable or inflatable structure. For example, as shown in FIG. 3, the medical device 10 may include one or more elongate bodies 44, 44' movably positioned within the catheter in a desired configuration, with the elongate bodies 44, 44' potentially experiencing axial movement and/or changes in tension when the device is in use.

Figure 4:
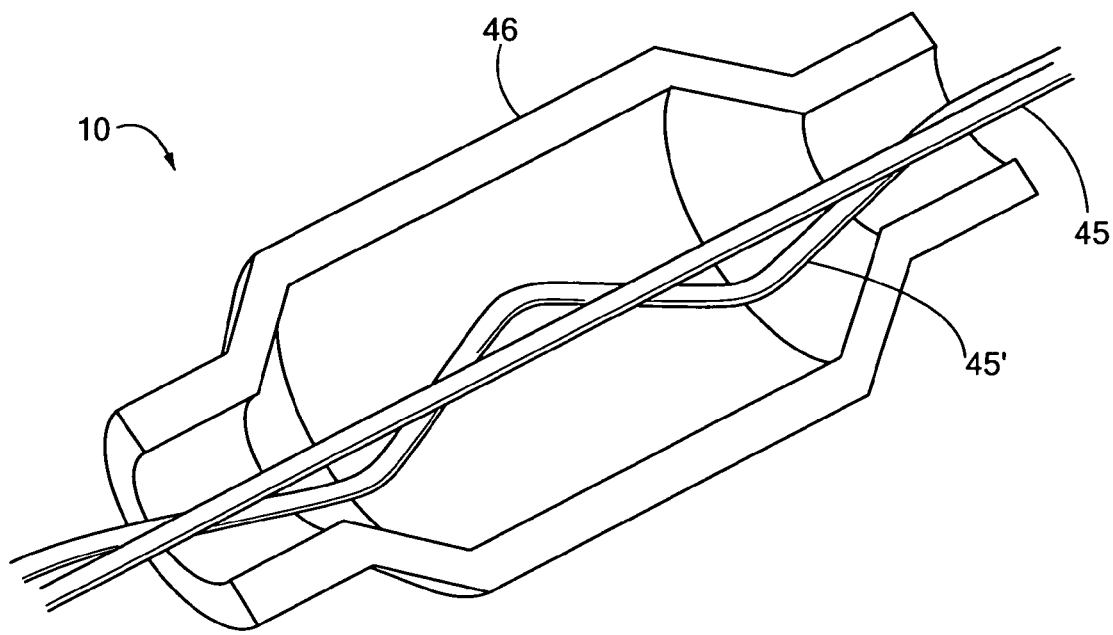
FIG. 4 provides another cross-sectional view of an embodiment of a medical device in accordance with the present invention.

Now referring to FIG. 4, the medical device 10 of the present invention may include a housing 46 for managing and accommodating lengths of one or more elongate bodies 45, 45', including guidewires, fluid supply tubes, as well as other fluid, electrical, and/or mechanical tubing or wiring employed in the medical device 10. The housing 46 may allow for the substantially unrestricted movement of one or more elongate bodies by providing a cavity or interior space to accommodate excess lengths of the one or more elongate bodies. For example, the housing 46 may have a larger inner diameter than other portions of the medical device 10. As such, should an elongate body at least partially disposed within the housing 46 experience some slack or other circumstance that causes the elongate body to retract or to "bunch up," the housing 46 provides room for the elongate body to do so while reducing the likelihood that the elongate body contacts an outer wall with such force as to cause kinking, bending, or other undesired results.

Figure 5:
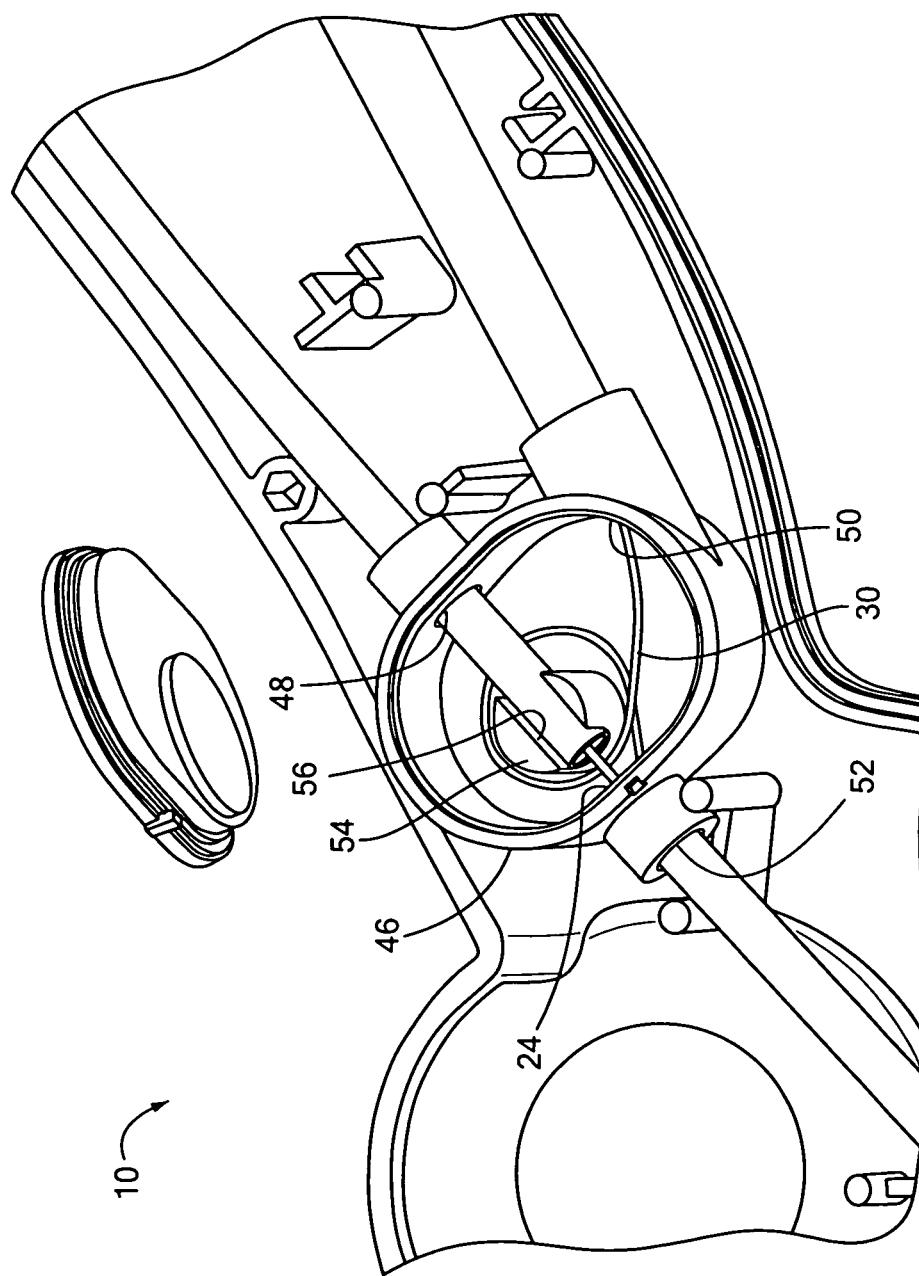
FIG. 5 shows an additional cross-sectional view of an embodiment of a medical device in accordance with the present invention.
Figure 6:
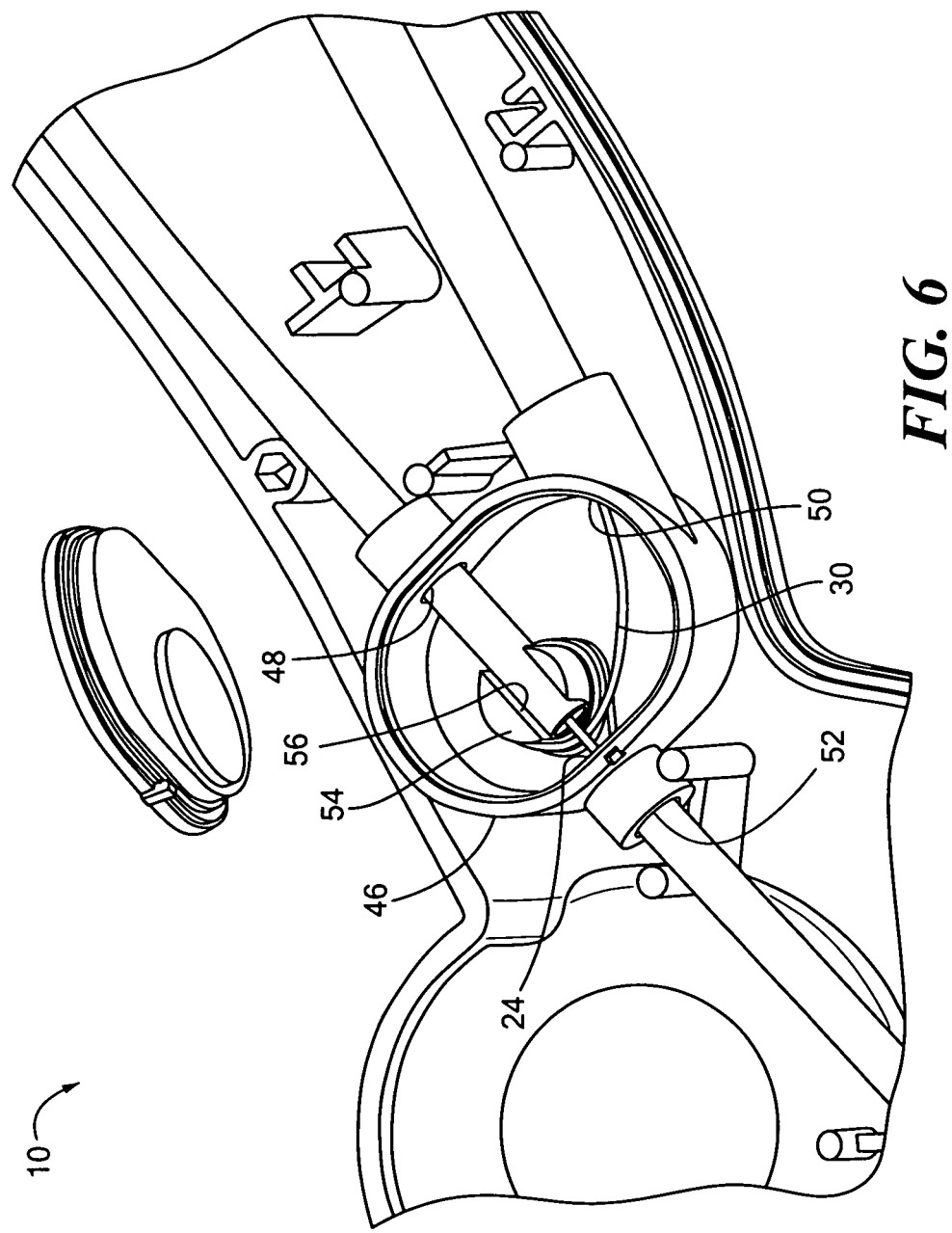
FIG. 6 shows yet another cross-sectional view of an embodiment of a medical device in accordance with the present invention.

Now referring to FIGS. 5 and 6, the medical device 10 of the present invention may include a housing 46 having a substantially rounded shape. The housing 46 may be disposed within the handle 16, and may include a first opening 48 for receiving the first elongate body 24, such as a portion of a guidewire lumen, as well as a second opening 50 for receiving the second elongate body 30, such as a portion of the fluid supply tube. The first and second openings may receive portions of the first and second elongate bodies from a proximal end of the handle 16. The housing 46 may further define a third opening 52 opposite the first and second openings for routing the first and second elongate bodies toward the distal end of the handle 16 and towards the catheter. Although not shown, the housing 46 may include numerous additional openings for routing and/or managing additional lengths of elongate bodies disposed within the medical device 10.

A separation element 54 may be disposed within the housing 46, such that a portion of the second elongate body 30 may be wrapped around the separation element 54 prior to exiting the housing 46 through the third opening 52. The separation element 54 increases the likelihood that a portion of the second elongate body 30 remains in a looped-orientation such that tension or axial movement experienced by the second elongate body 30 does not cause the second elongate body 30 to kink or otherwise bend at an undesirable angle. For example, the separation element 54 may include a post or other structure having a width, thereby maintaining a spacing or diameter of the looped portion of the second elongate body 30. The width of the separation element 54 may be larger than a minimum bend or kink radius of the second elongate body 30, which may depend on the particular material from which the second elongate body 30 is constructed.

In addition, the separation element 54 may include a path 56 for receiving a portion of the first elongate body 24, thereby guiding the first elongate body 24 towards the third opening 52. The path 56 may be displaced from a portion of the separation element 54 about which the second elongate body 30 is looped around, thereby providing a spacing between the first and second elongate bodies within the housing 46. The path 56, for example, may include a channel, groove, depression, aperture or similar passage in the body of the separation element 54. Although not shown, the separation element 54 may include multiple paths for additional elongate bodies coupled to the medical device 10 to aid in managing and routing multiple elongate bodies through the length of the medical device 10 to reduce the likelihood of tangling, kinking, or the like.

Moreover, a portion of the separation element 54 may be rotatably coupled to the housing 46 upon which lengths of an elongate body may be wound as to provide a reel of reserve elongate body length, as shown in FIG. 6. Upon experiencing tension along the second elongate body 30, the separation element 54 may rotate, thereby dispensing additional lengths of an elongate body as needed. The separation element 54 may further include a biasing element (not shown) such as a spring or other mechanism as known in the art, such that the separation element 54 automatically takes up additional slack by rotating and thus winding excess lengths of an elongate body about the separation element 54 when there is a reduced amount of tension experienced along the conduit length.

In an exemplary use of an embodiment of the medical device 10 of the present invention during a medical procedure, the first elongate body 24, such as a guidewire lumen, is routed through the first opening 48 of the housing 46, directed through the channel of the separation element 54, and directed out of the housing 46 and towards the distal end of the catheter through the third opening 52 of the housing 46. In addition, the second elongate body 30, such as a fluid supply tube, is routed into the housing 46 through the second opening 50 to form a loop around the separation element 54, and subsequently directed out of the housing 46 and towards the distal end of the catheter through the third opening 52.

During the medical procedure, the first elongate body 24 may be experience axial movement, such as through manipulation of the actuator element 42. The axial movement may be employed to provide a particular desired balloon shape, may be as a result of the particular level of inflation of the expandable element 14, or may be as a result of the insertion of a guidewire through the guidewire lumen. Irrespective of the cause, as a result of the movement of the first elongate body 24 and, thus, the expandable element 14, the second elongate body 30 will experience axial movement as well. As previously discussed, however, the spatial relationship between the second elongate body 30 and the expandable element 14 will remain substantially fixed in a pre-determined position to achieve a desired result or to employ a particular procedure. As a result, regardless of the particular orientation of the balloon and the first elongate body 24 during a stage of a procedure, i.e., an inflated state or uninflated state or transitioning in between, the second elongate body 30 may remain in a desired spatial relationship with the expandable element 14. Maintenance of the spatial relationship may, for example, provide a desired directed fluid flow, provide a desired thermal affect on a particular portion of the expandable element 14, or the like.

Figure 7:
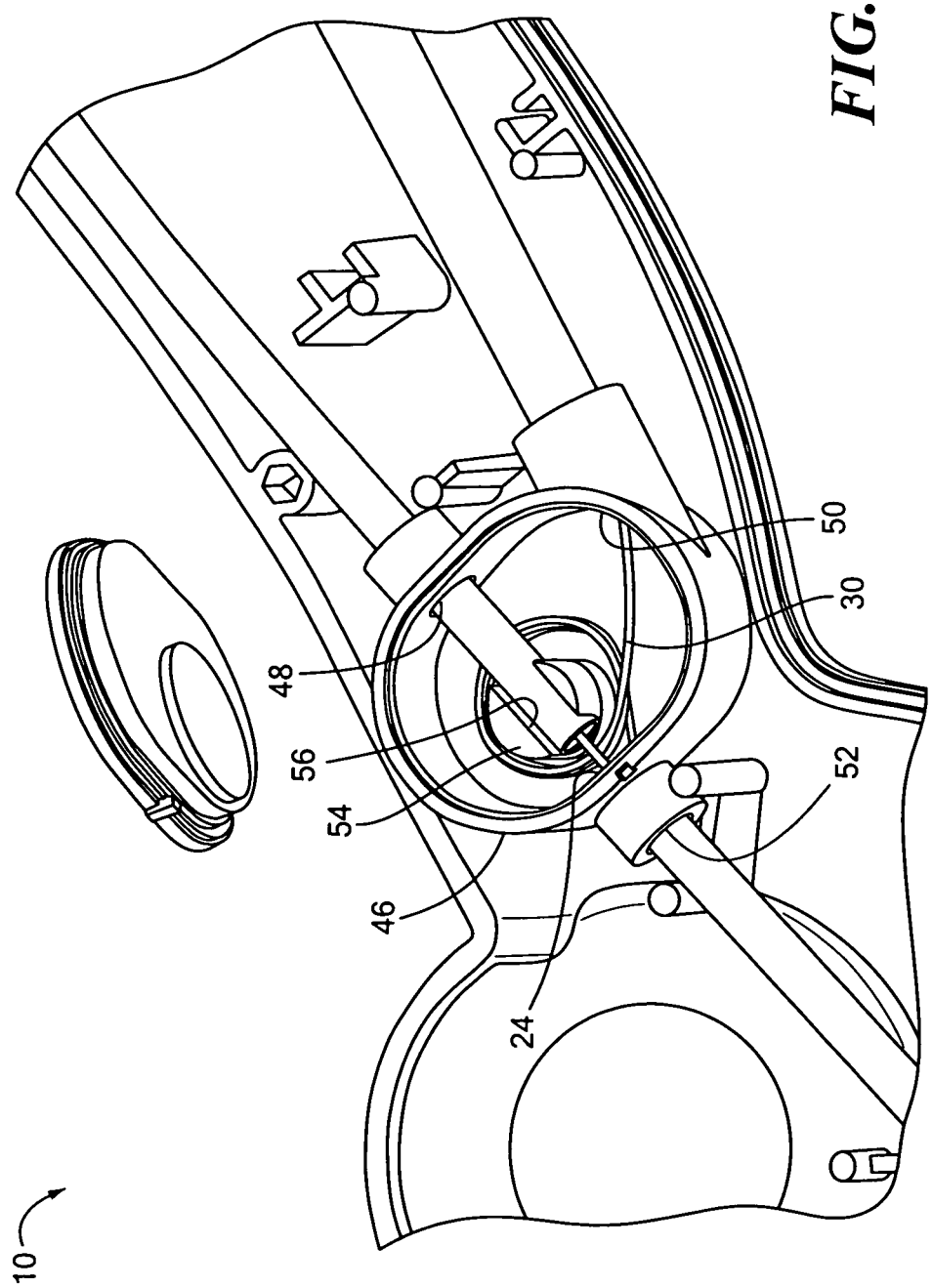
FIG. 7 provides an additional cross-sectional view of an embodiment of a medical device in accordance with the present invention.

Moreover, the slackened length of the second elongate body 30 will be taken up in the looped-portion of the conduit in the housing 46, i.e., an increase in the diameter of the looped portion will occur as shown in FIG. 7, thereby preventing kinking, as well as reducing any excess force on the medical device 10 that may cause a shift in positioning. Alternatively, should the separation element 54 be rotatably coupled to the housing 46, the slackened length of the second elongate body 30 may be taken up by rotating the separation element 54 either automatically or manually, as described above. Should the housing 46 include a substantially rounded shape, the expanded loop-portion of the second elongate body 30 may expand to a width of the housing 46 without contacting an angled surface which could cause kinking or bending of the first elongate body 24. In addition, the separate inlet portions of the housing 46 allow for separate and independent routing of the first and second elongate bodies, allowing for ease of connectability and manipulation of the individual elongate bodies and their connection points to the console 38, for example.

Although an embodiment of a medical device 10 in accordance with the present invention has been discussed and illustrated as possibly including an expandable or inflatable element, such as a balloon, it is intended and contemplated that elements of the present invention may be suitable for use in any device having one or more elongate bodies that may experience an axial movement or change in tension during use.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
    a catheter body defining a proximal portion and a distal portion;
    an expandable element coupled to the distal portion of the catheter body;
    a first elongate body movably disposed within the catheter body; and
    a fluid supply tube movably disposed within the catheter body, wherein the fluid supply tube is immovably affixed to the first elongate body at a location having a pre-determined spatial relationship to the expandable element, wherein the spatial relationship between the fluid supply tube and a portion of the expandable element is substantially maintained in an inflated state and an uninflated state of the expandable element.

2. The medical device according to claim 1, wherein the first elongate body defines a lumen able to receive a guidewire therein.

3. The medical device according to claim 1, wherein the fluid supply tube defines a plurality of apertures for releasing a fluid.

4. The medical device according to claim 1, further comprising a handle coupled to the proximal portion of the catheter body.

5. The medical device according to claim 4, further comprising an actuator element movably coupled to the handle.

6. The medical device according to claim 5, wherein the actuator element is coupled to the first elongate body.

7. The medical device according to claim 1, further comprising a console in communication with the fluid supply tube.

8. The medical device according to claim 1, further comprising:
    a housing, and a separation element having a width disposed within the housing, wherein the fluid supply tube forms a loop around at least a portion of the separation element.

9. The medical device according to claim 8, wherein the first elongate body is at least partially disposed within the housing.

10. The medical device according to claim 8, wherein the separation element defines a path able to receive a portion of the first elongate body.

11. The medical device according to claim 8, wherein the housing defines a first opening for receiving a portion of the first elongate body, a second opening for receiving a portion of the fluid supply tube, and a third opening opposite the first and second openings, wherein the third opening is able to receive a portion of both the first elongate body and the fluid supply tube.

12. The medical device according to claim 8, wherein at least a portion of the separation element is rotatable with respect to the housing.

13. A medical device, comprising:
    a catheter body defining a proximal portion and a distal portion;
    a guidewire lumen movably disposed within the catheter body, the guidewire lumen defining a distal portion and a proximal portion;
    an expandable element defining a proximal portion and a distal portion, wherein the proximal portion of the expandable element is coupled to the distal portion of the catheter body, and the distal portion of the expandable element is coupled to the distal portion of the guidewire lumen; and
    a fluid injection tube movably disposed within the catheter body, the fluid injection tube defining a distal portion and a proximal portion, wherein the distal portion of the fluid injection tube is securely affixed to the distal portion of the guidewire lumen in between the proximal and distal portions of the expandable element at a pre-determined position with respect to the expandable element to substantially maintain a spatial relationship between the distal portion of the fluid injection tube and the distal portion of the expandable element in both an inflated state and an uninflated state of the expandable element.

14. The medical device according to claim 13, further comprising a console in communication with the fluid injection tube.

* * * * *